United States Patent [19]

Spiering et al.

[11] Patent Number: 6,020,587
[45] Date of Patent: *Feb. 1, 2000

[54] PLANT CHLOROPHYLL CONTENT METER

[75] Inventors: Bruce A. Spiering; Gregory A. Carter, both of Long Beach, Miss.

[73] Assignee: United States of America as represented by the Administrator of the National Aeronautics and Space Administration, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 09/003,212

[22] Filed: Jan. 6, 1998

[51] Int. Cl.[7] .................................................. G01N 21/35
[52] U.S. Cl. ........................ 250/339.11; 356/419
[58] Field of Search ..................... 356/402, 416, 356/419; 250/339.11

[56] References Cited

U.S. PATENT DOCUMENTS

| | | | |
|---|---|---|---|
| 4,204,950 | 5/1980 | Burford et al. | 209/558 |
| 4,225,242 | 9/1980 | Lane | 356/407 |
| 4,295,042 | 10/1981 | Wantanabe et al. | 250/226 |
| 4,650,336 | 3/1987 | Moll | 356/417 |
| 4,804,850 | 2/1989 | Norrish et al. | 250/459 |
| 4,986,665 | 1/1991 | Yamanishi et al. | 356/402 |
| 5,014,225 | 5/1991 | Vidaver et al. | 364/550 |
| 5,353,053 | 10/1994 | Nishioka et al. | 348/33 |
| 5,389,781 | 2/1995 | Beck et al. | 250/226 |
| 5,412,219 | 5/1995 | Chapplle et al. | 250/461.1 |
| 5,467,271 | 11/1995 | Abel et al. | 364/420 |
| 5,486,915 | 1/1996 | Jeffers et al. | 356/318 |
| 5,576,550 | 11/1996 | Koppikar | 250/459.1 |
| 5,606,821 | 3/1997 | Sajadi et al. | 47/1.7 |

FOREIGN PATENT DOCUMENTS

| | | | |
|---|---|---|---|
| 62-282243 | 12/1987 | Japan | 356/402 |
| 62-282244 | 12/1987 | Japan | 356/402 |
| 62-282245 | 12/1987 | Japan . | |

OTHER PUBLICATIONS

Carter, G., "Ratios of Leaf Reflections in Narrow Wavebands as Indicators of Plant Stress", *Int. J. Remote Sensing*, vol. 15, No. 3, 679–703, (1994).

Carter, G., et al., "Early Detection of Plant Stress by Digital Imaging Within Narrow Stress–Sensitive Wavebands", *Remote Sens. Environ* 50, 295–302, (1994).

Carter, G., et al., "Leaf Optical Properties in *Liriodendron tulipifera* and *Pinus strobus* as Influenced by Increased Atmospheric Ozone and Carbon Dioxide", *Can. J. For. Res.* 25, 407–412, (1995).

Carter, G., et al., "Narrow–Band Reflectance Imagery Compared with Thermal Imagery for Early Detection of Plant Stress", *L. Plant Physiol.* vol. 148, 515–522, (1996).

(List continued on next page.)

*Primary Examiner*—F. L. Evans
*Attorney, Agent, or Firm*—Beth A. Vrioni; Gary G. Borda

[57] ABSTRACT

A plant chlorophyll content meter is described which collects light reflected from a target plant and separates the collected light into two different wavelength bands. These wavelength bands, or channels, are described as having center wavelengths of 700 nm and 840 nm. The light collected in these two channels are processed using photo detectors and amplifiers. An analog to digital converter is described which provides a digital representation of the level of light collected by the lens and falling within the two channels. A controller provided in the meter device compares the level of light reflected from a target plant with a level of light detected from a light source, such as light reflected by a target having 100% reflectance, or transmitted through a diffusion receptor. The percent of reflection in the two separate wavelength bands from a target plant are compared to provide a ratio which indicates a relative level of plant physiological stress. A method of compensating for electronic drift is described where a sample is taken when a collection lens is covered to prevent light from entering the device. This compensation method allows for a more accurate reading by reducing error contributions due to electronic drift from environmental conditions at the location where a hand-held unit is used.

28 Claims, 2 Drawing Sheets

OTHER PUBLICATIONS

Carter, G., et al., "Spectral Reflectance Characteristics and Digital Imagery of a Pine Needle Blight in the Southeastern United States", *Can. J. For. Res.* 26, 402–407, (1996).

Carter, G.A., "Responses of Leaf Spectral Reflectance to Plant Stress", *American Journal of Botany*, 239–243, (Mar. 1993).

Cibula, W.G., et al., "Identification of Far–Red Reflectance Response to Ectomycorrhizae in Slash Pine", *Int. J. Remote Sensing*, vol. 13, No. 5, 925–932, (1992).

Gitelson et al, Novel Algorithms for Remote Sensing of Chlorophyll Content in Higher Plant Leaves, a paper appearing in Geoscience and Remote Sensing Symposium, 1996, IGARSS '96, 'Remote Sensing for a Sustainable Future.' International on pp. 2355–2357 (abstract only), 1996.

PLANT CHLOROPHYLL CONTENT METER

TECHNICAL FIELD OF THE INVENTION

The present invention relates generally to plant chlorophyll content meters and in particular the present invention relates to a device which measures chlorophyll content in a plant using light reflectance.

BACKGROUND OF THE INVENTION

Early detection of vegetation physiological stress is beneficial to the environmental and agricultural business community. Plant stresses can be a result of numerous influences including but not limited to drought, chemicals such as herbicides, or biological influences. Early detection can provide an opportunity to reverse the physiological stress or at least identify that stress is present. When unfavorable growth conditions result in plant physiological stress, leaf chlorophyll content typically begins to decrease. Consequently, methods of detecting the content of leaf chlorophyll provide a measure or indication of a level of such stress.

Different approaches to plant stress detection by measuring leaf chlorophyll are available. One such technique which can be used is fluorescence. In the case of fluorescence, incident light is absorbed by leaf pigments. Not all of the absorbed light energy is transferred chemically to be used in photosynthesis. Rather, some of this absorbed energy is re-emitted, or fluoresced, by chlorophyll at far-red, or near-infrared wavelengths. Maximum chlorophyll fluorescence occurs at wavelengths near 690 and 730 nm. For this reason, fluorometers often measure fluorescence with narrow bands centered near 690 or 730 nm. In general, fluorescence in these bands tends to increase with decreased chlorophyll content or increased degree of physiological stress. To measure far-red or near-infrared fluorescence, the leaf is irradiated only with light of much shorter wavelengths (e.g., blue or green light). This insures that any far-red or near-infrared light emanating from the leaf is indeed fluorescence and not merely incident light that has been reflected by the leaf.

A second method of measuring plant chlorophyll content is through the use of transmittance. This technique transmits light through a leaf of a target plant. A percent of light transmitted through the leaf at specific wavelengths is measured. These wavelengths are typically 650 nm and 940 nm. As chlorophyll content changes, the ratio of transmittance at these wavelengths changes. A clear defect in monitoring plant chlorophyll content using this method is the requirement of physical contact with a plant leaf.

Another approach to detecting physiological plant stress by measuring leaf chlorophyll is accomplished by monitoring the reflection of incident light. Reflectance of incident radiation from the leaf interior increases as plant chlorophyll decreases, providing an optical indicator of stress. Reflectance sensitivity analysis has shown that increased reflectance in specific wavebands provides an early and more consistent indication of stress than reflectance at other wavelengths as a result of the absorption properties of chlorophyll. Depending on the severity of stress, this reflectance response can be detected prior to damage symptoms apparent to the unaided eye. Reflectance has been shown to detect decreased chlorophyll content by at least sixteen days prior to visual indications such as leaf color changes. Reflectance measurements are typically made while the plant leaf is exposed to a full incident spectrum from the sun, or an artificial light source. Although some fluoresced energy must also be measured in combination with reflected light, the fluoresced energy is small compared with a greater intensity of reflected light. Further, physical contact with the target plant is not required.

Different techniques are known for conducting reflectance measurements to indicate plant stress. These techniques, however, require extensive field measurements combined with laboratory analysis of the collected measurements. For the reasons stated above, and for other reasons stated below which will become apparent to those skilled in the art upon reading and understanding the present specification, there is a need in the art for a simplified chlorophyll content meter which provides an indication of physiological stress in plants based on reflectance of incident light.

SUMMARY OF THE INVENTION

The above mentioned problems with detecting plant stress and other problems addressed by the present invention will be understood by reading and studying the following specification. A chlorophyll content meter is described which uses reflected light from a target plant at two wavelengths of light to detect chlorophyll content and provide an indication of plant stress.

In particular, the present invention describes a chlorophyll content meter comprising a first optical bandpass filter for filtering light received through an optical lens, and a second optical bandpass filter for filtering light received through an optical lens. The first bandpass filter transmits a central wavelength, and the second bandpass filter transmits a central wavelength. The chlorophyll content meter further comprises detector circuitry for detecting a level of light output from each of the first and second optical bandpass filters and converting the detected levels into a digital representation, and a controller for receiving the digital representations and calculating chlorophyll content of a target plant. The controller calculates a percent of light reflected from the target plant by comparing outputs from the first and second optical bandpass filter produced from light reflected from the target plant against outputs from the first and second optical bandpass filter produced from light detected from a light source.

In another embodiment, a hand-held light reflectance meter for use in measuring plant chlorophyll content comprises an optical lens for collecting light from a light source or reflected from a target plant under test, and an optical beam splitter for dividing light collected by the optical lens into first and second light beams. A first optical bandpass filter is provided for receiving the first light beam from the optical beam splitter and providing a light output having a center wavelength of approximately 700 nm. A first light detector is coupled to the first optical bandpass filter for providing an output indicating a level of the light output from the first optical bandpass filter. A second optical bandpass filter is provided for receiving the second light beam from the optical beam splitter and providing a light output having a center wavelength of approximately 840 nm. A second light detector is coupled to the second optical bandpass filter for providing an output indicating a level of the light output from the second optical bandpass filter. The hand-held light reflectance meter further comprises processing circuitry for converting the outputs from the first and second light detectors into a digital data representation, and a controller coupled to the processing circuitry for calculating plant chlorophyll content levels using digital data representing light reflected from the reference target and digital data representing light reflected from the target plant. The controller provides an output of light reflected from the target plant as a percent of the light reflected from the reference target. The controller also provides an output of the ratio of the percent of reflected light output by the first optical bandpass filter to the percent of reflected light output by the second optical bandpass filter. A display provides a user with the output from the controller.

In yet another embodiment, a method of detecting plant chlorophyll content for identifying early plant stress using a chlorophyll content meter is described. The method comprises the steps of detecting light from a light source having a first wavelength using the chlorophyll content meter, detecting light from the light source having a second wavelength using the chlorophyll content meter, detecting light reflected from a target plant having a first wavelength using the chlorophyll content meter, and detecting light reflected from the target plant having a second wavelength using the chlorophyll content meter. The method comprises the steps of calculating a first reflected percent of light reflected from the target plant having the first wavelength from the light detected from the light source having the first wavelength, and calculating a second reflected percent of light reflected from the target plant having the second wavelength from the light detected from the light source having the second wavelength. A ratio of the first reflected percent to the second reflected percent is calculated, and an output is provided which indicates a relative plant stress level based upon the calculated ratio.

DETAILED DESCRIPTION OF THE INVENTION

In the following detailed description of the preferred embodiments, reference is made to the accompanying drawings which form a part hereof, and in which is shown by way of illustration specific preferred embodiments in which the inventions may be practiced. These embodiments are described in sufficient detail to enable those skilled in the art to practice the invention, and it is to be understood that other embodiments may be utilized and that logical, mechanical and electrical changes may be made without departing from the present inventions. The following detailed description is, therefore, not to be taken in a limiting sense, and the scope of the present invention is defined only by the appended claims.

Figure 1:
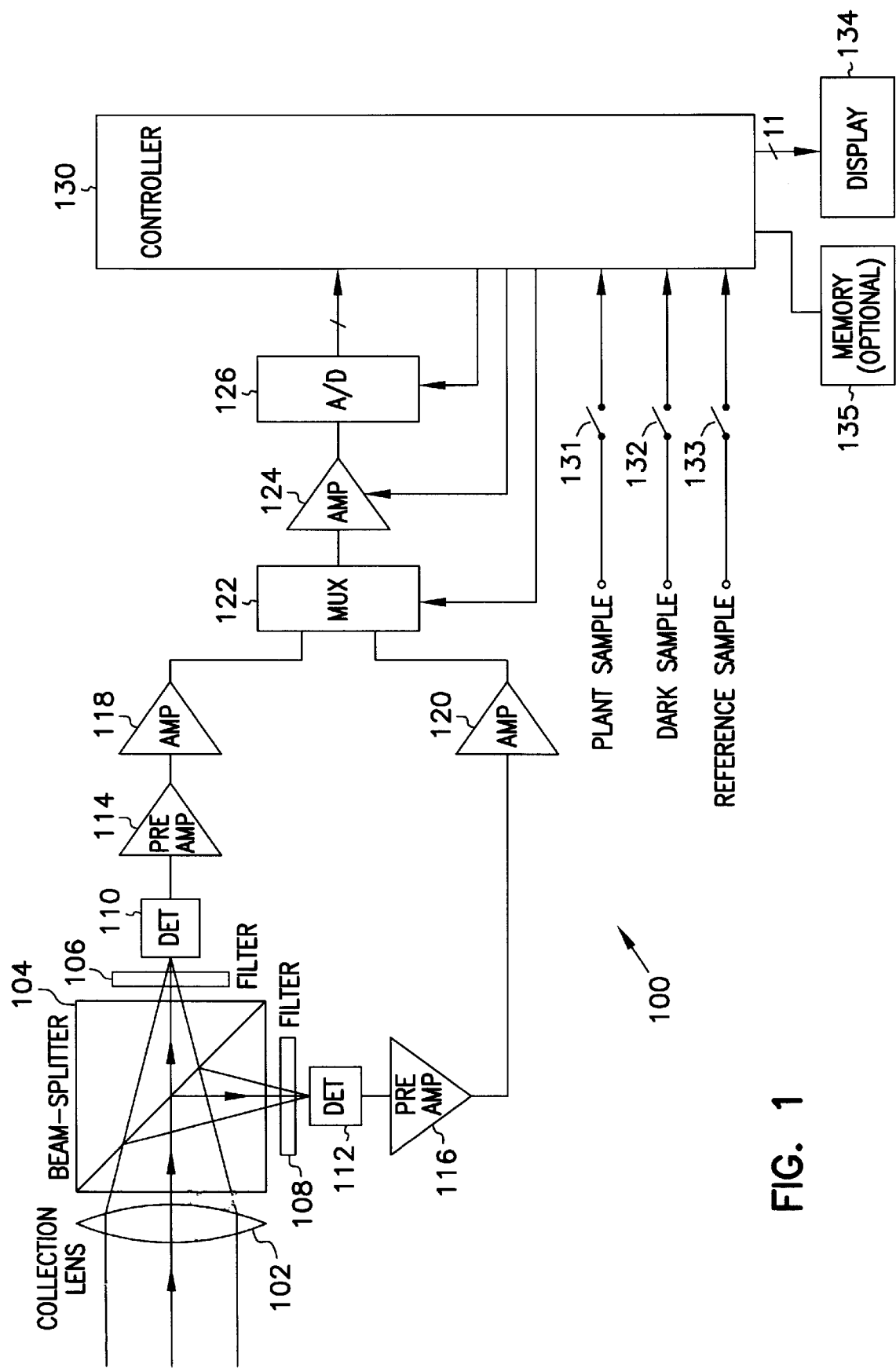
FIG. 1 is a schematic diagram of a meter device of the present invention using light reflectance.

Referring to FIG. 1, one embodiment of a chlorophyll content meter system of the present invention is described. The chlorophyll content meter measures light reflected from a plant in two different wavelength bands and compares the amount of light from these two bands to compute chlorophyll content. The meter compares the level of light reflected from a target plant in the two bands with a reference level of light in the two bands from a source illuminating the plant. The system provides an output indicating the relative plant stress level. The detection system is preferably embodied as a hand-held unit which is portable so that it can be used by an operator in the field for real time analysis of the condition of a plant.

The chlorophyll content meter 100 includes a collection lens 102 which collects light energy and focuses it on a beam splitter 104. The beam splitter is configured to split the collected light from the collection lens into equal parts (50/50) such that equal amounts of light are focused on bandpass filter 106 and bandpass filter 108. The beam splitter can be configured in different percentages, and is not limited to 50/50. Bandpass filter 106 allows infrared light having a wavelength in the range of 840±5 nm to pass through the filter to photo diode detector 110. Similarly, bandpass filter 108 allows red light having a wavelength in the range of 700±5 nm to pass through the filter to photo diode detector 112.

The light detectors 106 and 108 convert light to electric current which is converted to a voltage signal and amplified by respective pre-amplifiers 110 and 112. Additional gain/offset amplifier circuits 118 and 120 are provided for each preamplifier. These amplifiers allow for adjustment of gain to maximize an input range to analog-to-digital (A/D) converter 126 and eliminate any systematic signal offset. An analog 2:1 multiplexer circuit is provided to selectively couple an output signal from either gain/offset amplifier 118 or gain/offset amplifier 120 to a sample and hold amplifier 124. The sample and hold amplifier latches an output from the multiplexer until A/D converter 126 converts an analog voltage level to a digital, or numeric value. It will be understood that other circuits can be used to convert light from the two desired wavelength ranges into a digital representation. The circuit, therefore, can be varied without departing from the invention.

Microcontroller 130 controls multiplexer 122, sample and hold amplifier 124, and A/D converter 126 during operation. The microcontroller also monitors user input signals for collecting a reference light measurement, a dark reference measurement, or a reflectance measurement from a target plant. During operation, each of these measurements should be conducted to provide a reliable indication of chlorophyll content, or physiological plant stress, as explained in greater detail below. Display 134 provides a visible indication of reflected light levels, and a relative level of plant stress of a target plant. In one embodiment, the display illustrates an alphanumeric representation of a relative plant stress level. The level of reflected light in each bandpass channel can also be displayed on display 134. Further, different displays such as a band of LEDs or an analog meter could be used.

In operation, the chlorophyll content meter performs an analysis of the ratio of percent reflectance from two distinct wavelength channels. A sample of incident solar irradiance, or light source, reflected from a 100% reflectance target is used to compensate for variances of the source of light. The light source is used to illuminate a target plant(s) during testing. Further a dark sample can be taken and used to remove any drift in the electronics from thermal variations. This drift could be eliminated through the use of more sophisticated circuitry, or limiting use to specific thermal conditions.

In one operational embodiment of the present invention, the microcontroller begins execution upon power-up of the detector. The microcontroller then monitors the three user inputs until one is selected. A normal sequence of operation includes the input of a reference light level. The user, therefore, activates the reference sample input 133 and directs the collection lens 102 toward a white, or 100% reflectance, target. The microcontroller then collects 5 data samples of each channel from the optical system. That is, a plurality of samples are taken from each bandpass filter. The samples can be taken in an alternate fashion, such that a sample is first taken from filter 106 and a subsequent sample from filter 108, and then back to filter 106. The samples of each wavelength are averaged, and stored in the microcontroller, or optional memory 135, for later use.

Alternately, the reference light level can be collected by directing the lens of the meter toward a light source. To prevent possible damage to the meter, a diffusion receptor is placed in front of the lens. This diffusion receptor, or cosine receptor, allows the detection of light from the light source in the two desired wavelengths for reference levels. In one embodiment, a white translucent material is placed in front of the lens while the meter is pointed at the light source (sun, lamp, ect.). The level of transmittance of the receptor is known, and is used to convert the measured light to levels which would be measured using a 100% reflective target. The light detected by each detector 106 and 108 is adjusted accordingly by the microcontroller.

A user then activates the plant sample input 131 to measure chlorophyll content or physiological stress of a target plant and directs the collecting lens toward the target plant. The microcontroller then collects five sample light reflectances from each bandpass filter and averages the samples in the same manner as described above for the reference sample. A percent reflectance is computed for each wavelength by dividing the sample of the target plant by a respective reflectance of the wavelength from the stored reference sample. For example, the average reflectance measured by bandpass filter 106 as collected from a target plant is divided by the average reflectance measured by bandpass filter 106 as collected from the 100% reflectance target. Finally, the level of plant stress is computed by dividing the 700 nm percent reflectance by the 840 nm percent reflectance. The result is displayed on display 134 until the next sample is taken. The ratio of percent reflectance for the two wavelengths ranges from approximately 0.1 for a healthy plant to 0.4 and greater for an unhealthy plant. It will be understood that these ratios can vary for different plant species. As such, a ratio below 0.2 generally indicates a healthy plant, while a ratio above 0.25 generally indicates an unhealthy plant. Optionally, reflectance levels and the ratio of reflectances can be stored in memory for later retrieval and analysis.

The dark sample can be taken as often as necessary with an opaque cover placed over the collection lens 102. This dark sample reading is stored until re-selected using input 132 and is subtracted from the reflectance measurements to compensate for error contributions due to circuit drift. The dark sample is taken and averaged for each wavelength in the same manner as described above.

Figure 2:
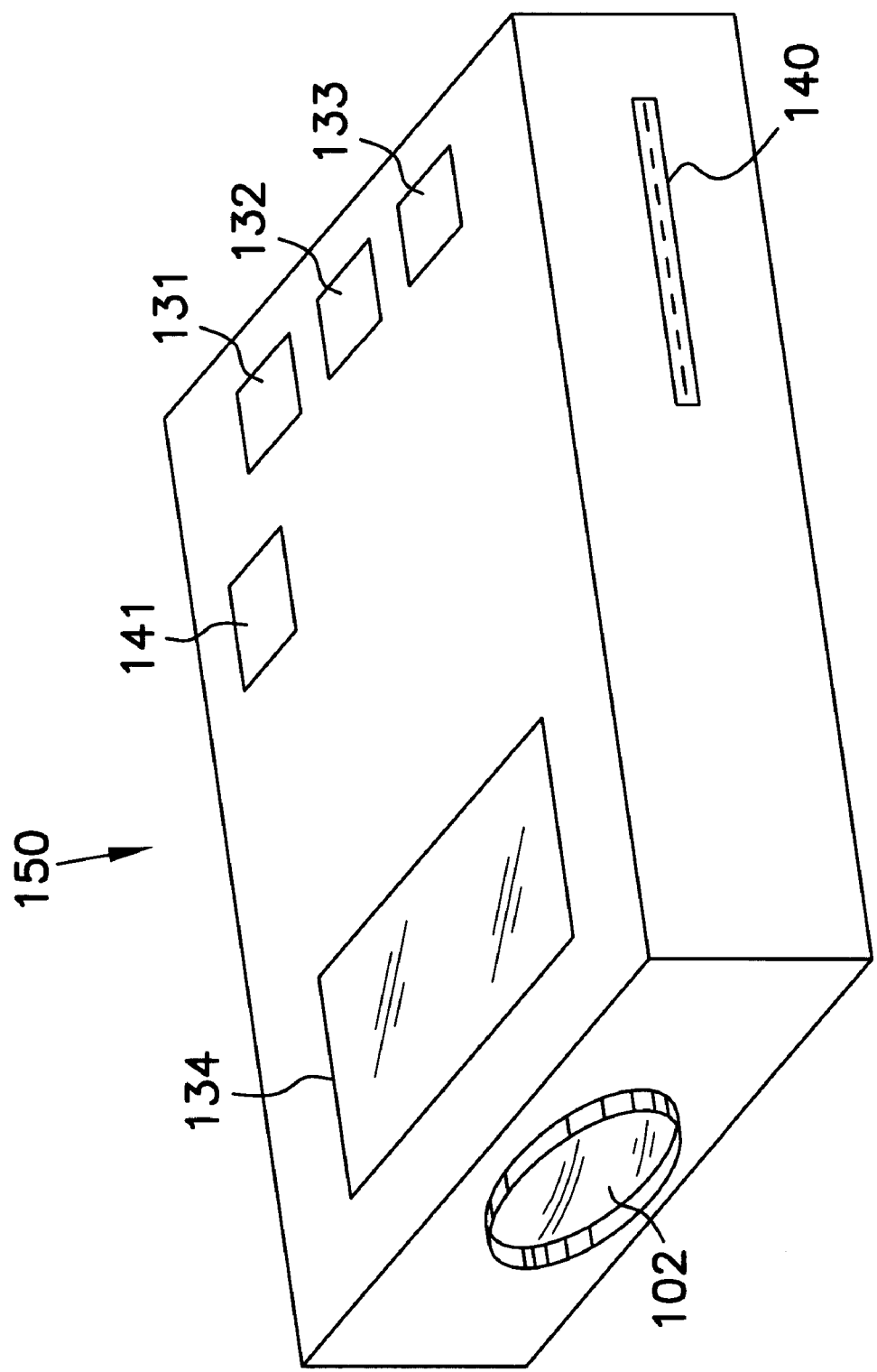
FIG. 2 illustrates an embodiment of a hand held meter of the present invention.

Referring to FIG. 2, one embodiment of a hand-held plant chlorophyll content meter incorporating the circuitry of FIG. 1 is described. The hand-held meter 150 includes a collection lens 102 for collecting light, input switches 131, 132 and 133 for controlling operation of the meter as described above. The meter also includes alphanumeric display 134 which provides a user with a status of the operation of the meter, and also a representation of the reflectance levels measured. As explained above, the reflectance levels for both wavelength ranges can be displayed, along with a ratio of the reflectance levels to indicate a level of plant stress. A power control switch 141 is provided for activating the meter, and an optional data communication connection 140 can be provided for communicating with microcontroller 130 or optional memory 135. Other standard features of the meter, such as a power supply, are not described in detail herein, but are anticipated to be within the teachings of those skilled in the art.

The hand-held meter has been designed to allow a user to easily carry the meter and take measurements of plant chlorophyll in a location where the plant is growing. As such, real-time analysis is possible. Further, physical contact with the plant is not necessary as with transmittance-based instrumentation. The present invention can be used by biologists or agriculturalists to assist in indicating any species of plant which may be suffering from stress due to a variety of causes. Although the present invention does not identify the cause of such stress, it is believed that early detection of plant stress provides options not available if plant stress is not detected until visual indications are present.

A field test of the present invention was conducted on grape plants. During the test, chlorophyll was extracted from grape leaves and compared with prior readings taken with the chlorophyll content meter using light reflectance from the plant leaves. The test revealed a statistical correlation where $r^2$ was greater than 0.9.

It will be appreciated by those skilled in the art that variations in the circuitry or construction of the chlorophyll content meter described herein are possible. For example, microcontroller 130 can include any type of microprocessor, ASIC, or programmable controller capable of performing the described algorithm for determining a percent of reflectance from a sample value against a reference value, and determining a ratio of two reflectance values. Further, variations in the optical filter wavelengths are contemplated. The described center wavelengths of 700 and 840 nm, however, are preferred and believed to provide the best indication of early chlorophyll content loss. Further, although one collection lens 102 has been described, it will be appreciated that two collection lenses could be used in combination with separate bandpass filters to measure reflected light.

Conclusion

A plant chlorophyll content meter has been described which collects light reflected from a target plant and separates the collected light into two different wavelength bands. These wavelength bands, or channels, are described as having center wavelengths of 700 nm and 840 nm. The light collected in these two channels is processed using photo detectors and amplifiers. An analog to digital converter has been described which provides a digital representation of the level of light collected by the lens and falling within the two channels. A controller provided in the meter device compares the level of light reflected from a target plant with a reference level of light from a source illuminating the plant. The reference can be measured using reflectance, such as from a white target having 100% reflectance. The percent of reflection in the two separate wavelength bands from a target plant are compared to provide a ratio which indicates a relative level of plant physiological stress. A method of compensating for electronic drift is described where a sample is taken when a collection lens is covered to prevent light from entering the device. This compensation method allows for a more accurate reading by reducing error contributions due to electronic drift from environmental conditions at the location where a hand-held unit is used.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is manifestly intended that this invention be limited only by the claims and the equivalents thereof.

What is claimed is:

1. A chlorophyll content meter comprising:
   a first optical bandpass filter for filtering light received through an optical lens, the first bandpass filter having a central wavelength of transmission of 700 nm;

a second optical bandpass filter for filtering light received through an optical lens, the second bandpass filter having a central wavelength of transmission of 840 nm;

detector circuitry for detecting a level of light output from each of the first and second optical bandpass filters and converting the detected levels into digital representations; and a controller for receiving the digital representations and calculating a relative chlorophyll content of a target plant, whereby the controller calculates a percent of light reflected from the target plant by comparing outputs from the first and second optical bandpass filter produced from light reflected from the target plant against outputs from the first and second optical bandpass filter produced from a light source.

2. The chlorophyll content meter of claim 1 further comprising an alphanumeric display for providing visual output indicating a content level of chlorophyll of the target plant.

3. The chlorophyll content meter of claim 1 wherein the controller calculates a ratio of the percent reflectance of the target plant as output by the first optical bandpass filter to the percent reflectance of the target plant as output by the second optical bandpass filter.

4. The chlorophyll content meter of claim 1 wherein the detector circuitry comprises:

a first detector circuit for detecting light output from the first optical bandpass filter;

a second detector circuit for detecting light output from the second optical bandpass filter;

a first amplifier circuit for amplifying an output from the first detector circuit;

a second amplifier circuit for amplifying an output from the second detector circuit; and an analog to digital converter circuit for converting outputs from the first and second amplifier circuits to digital data.

5. The chlorophyll content meter of claim 4 wherein the detector circuitry further comprises a multiplex circuit for selectively coupling outputs from the first and second amplifier circuits with the analog to digital converter.

6. The chlorophyll content meter of claim 1 further comprising a memory circuit coupled to the controller for storing data representing output from the first and second bandpass filters produced from light reflected from a reference target for use by the controller.

7. The chlorophyll content meter of claim 1 wherein light from the light source is collected from a reflective target to produce the outputs from the first and second optical bandpass filters.

8. A hand-held light reflectance meter for use in measuring plant chlorophyll content comprising:

an optical lens for collecting light from a light source or reflected from a target plant under test;

an optical beam splitter for dividing light collected by the optical lens into first and second light beams;

a first optical bandpass filter for receiving the first light beam from the optical beam splitter and providing a light output having a center wavelength of approximately 700 nm;

a first light detector coupled to the first optical bandpass filter for providing an output indicating a level of the light output from the first optical bandpass filter;

a second optical bandpass filter for receiving the second a light beam from the optical beam splitter and providing a light output having a center wavelength of approximately 840 nm;

a second light detector coupled to the second optical bandpass filter for providing an output indicating a level of the light output from the second optical bandpass filter;

processing circuitry for converting the outputs from the first and second light detectors into a digital data representation;

a controller coupled to the processing circuitry for calculating plant chlorophyll content levels using digital data representing light from the light source and digital data representing light reflected from the target plant, the controller providing an output of light reflected from the target plant as a percent of the light from the light source, and the controller providing an output of the ratio of the percent of reflected light output by the first optical bandpass filter to the percent of reflected light output by the second optical bandpass filter; and a display for providing a user with the output from the controller.

9. The hand-held light reflectance meter of claim 8 further comprising a memory for storing data representing light reflected from a reference target.

10. The hand-held light reflectance meter of claim 9 wherein the memory further stores data representing an offset value for use in compensating for variables due to electronic drift resulting from thermal variations.

11. The hand-held light reflectance meter of claim 8 wherein the controller compensates for variables due to electronic drift resulting from thermal variations.

12. The hand-held light reflectance meter of claim 8 further comprising input controls for controlling operation of the reflectance meter.

13. The hand-held light reflectance meter of claim 8 wherein the processing circuitry comprises a multiplex circuit for selectively coupling the outputs from the first and second light detectors to the controller.

14. The hand-held light reflectance meter of claim 8 wherein the first and second optical bandpass filters each have a bandwidth of 10 nm.

15. The hand-held light reflectance meter of claim 8 wherein light from the light source is collected from a reflective target.

16. A method of detecting plant chlorophyll content for identifying early plant stress using a chlorophyll content meter, the method comprising:

detecting light from a light source having a first wavelength of 700 nm using the chlorophyll content meter;

detecting light from the light source having a second wavelength of 840 nm using the chlorophyll content meter;

detecting light reflected from a target plant having a first wavelength using the chlorophyll content meter;

detecting light reflected from the target plant having a second wavelength using the chlorophyll content meter;

calculating a first reflected percent of light reflected from the target plant having the first wavelength from the light detected from the light source having the first wavelength;

calculating a second reflected percent of light reflected from the target plant having the second wavelength from the light detected from the light source having the second wavelength;

calculating a ratio of the first reflected percent to the second reflected percent; and providing an output indicating a relative plant stress level based upon the calculated ratio.

17. The method of claim 16 wherein each of the steps of detecting light comprises:

collecting reflected light using an optical lens;

filtering the collected light using an optical bandpass filter having a pre-selected bandwidth;

detecting an output level of light passing through the optical bandpass filter; and converting the detected output level into a digital data value.

18. The method of claim 16 wherein a low ratio indicates a low level of plant stress, and a high ratio indicates a high level of plant stress.

19. The method of claim 16 wherein the light detected from the light source is reflected from a target which substantially reflects 100 percent of light provided by a light source.

20. A chlorophyll content meter comprising:

a first optical bandpass filter for filtering light received through an optical lens, the first bandpass filter having a central wavelength of transmission of 700 nm;

a second optical bandpass filter for filtering light received through an optical lens, the second bandpass filter having a central wavelength of transmission;

detector circuitry for detecting a level of light output from each of the first and second optical bandpass filters and converting the detected levels into digital representations; and a controller for receiving the digital representations and calculating a relative chlorophyll content of a target plant, whereby the controller calculates a percent of light reflected from the target plant by comparing outputs from the first and second optical bandpass filter produced from light reflected from the target plant against outputs from the first and second optical bandpass filter produced from a light source, wherein the controller calculates a ratio of the percent reflectance of the target plant as output by the first optical bandpass filter to the percent reflectance of the target plant as output by the second optical bandpass filter.

21. The chlorophyll content meter of claim 20 wherein the central wavelength of transmission of the second optical bandpass filter is 840±5 nm.

22. The chlorophyll content meter of claim 20 further comprising an alphanumeric display for providing visual output indicating a content level of chlorophyll of the target plant.

23. The chlorophyll content meter of claim 20 wherein the detector circuitry comprises:

a first detector circuit for detecting light output from the first optical bandpass filter;

a second detector circuit for detecting light output from the second optical bandpass filter;

a first amplifier circuit for amplifying an output from the first detector circuit;

a second amplifier circuit for amplifying an output from the second detector circuit; and an analog to digital converter circuit for converting outputs from the first and second amplifier circuits to digital data.

24. A method of detecting plant chlorophyll content for identifying early plant stress using a chlorophyll content meter, the method comprising:

detecting light from a light source having a first wavelength of 700 nm using the chlorophyll content meter;

detecting light from the light source having a second wavelength using the chlorophyll content meter;

detecting light reflected from a target plant having a first wavelength using the chlorophyll content meter;

detecting light reflected from the target plant having a second wavelength using the chlorophyll content meter;

calculating a first reflected percent of light reflected from the target plant having the first wavelength from the light detected from the light source having the first wavelength;

calculating a second reflected percent of light reflected from the target plant having the second wavelength from the light detected from the light source having the second wavelength;

calculating a ratio of the first reflected percent to the second reflected percent; and providing an output indicating a relative plant stress level based upon the calculated ratio.

25. The method of claim 24 detecting light comprises:

collecting reflected light using an optical lens;

filtering the collected light using an optical bandpass filter having a pre-selected bandwidth;

detecting an output level of light passing through the optical bandpass filter; and converting the detected output level into a digital data value.

26. The method of claim 24 wherein a low ratio indicates a low level of plant stress, and a high ratio indicates a high level of plant stress.

27. The method of claim 24 wherein the light detected from the light source is reflected from a target substantially reflects 100 percent of light provided by a light source.

28. The method of claim 24 wherein the second wavelength is 840±5 nm.

* * * * *